(12) United States Patent
Choa et al.

(10) Patent No.: US 11,056,559 B2
(45) Date of Patent: Jul. 6, 2021

(54) GAS SENSOR AND METHOD FOR MANUFACTURING SAME

(71) Applicant: INDUSTRY-UNIVERSITY COOPERATION FOUNDATION HANYANG UNIVERSITY ERICA CAMPUS, Ansan-si (KR)

(72) Inventors: Yong Ho Choa, Ansan-si (KR); Nu Si A Eom, Pyeongtaek-si (KR); Hyo Ryoung Lim, Ansan-si (KR); Yoseb Song, Ansan-si (KR)

(73) Assignee: INDUSTRY-UNIVERSITY COOPERATION FOUNDATION HANYANG UNIVERSITY ERICA CAMPUS, Ansan-si (KR)

( * ) Notice: Subject to any disclaimer, the term of this patent is extended or adjusted under 35 U.S.C. 154(b) by 0 days.

(21) Appl. No.: 16/538,157

(22) Filed: Aug. 12, 2019

(65) Prior Publication Data

US 2019/0360958 A1 Nov. 28, 2019

Related U.S. Application Data

(63) Continuation of application No. PCT/KR2018/002927, filed on Mar. 13, 2018.

(30) Foreign Application Priority Data

Mar. 22, 2017 (KR) .......................... 10-2017-0035844

(51) Int. Cl.
*H01L 29/16* (2006.01)
*G01N 27/12* (2006.01)
(Continued)

(52) U.S. Cl.
CPC ....... *H01L 29/1606* (2013.01); *G01N 27/129* (2013.01); *G01N 27/4045* (2013.01);
(Continued)

(58) Field of Classification Search
CPC ........... G01N 27/4141; G01N 27/4146; G01N 27/4148; G01N 27/4045; G01N 27/4074;
(Continued)

(56) References Cited

U.S. PATENT DOCUMENTS 6,506,263 B1 * 1/2003 Basaly ................. C25D 11/246
148/272
8,487,296 B2 * 7/2013 Grebel .............. H01L 29/66742
257/20

FOREIGN PATENT DOCUMENTS

KR 10-2010-0092091 A 8/2010
KR 10-2011-0049673 A 5/2011
(Continued)

OTHER PUBLICATIONS

International Search Report issued in PCT/KR2018/002927; dated Jun. 14, 2018.

*Primary Examiner* — Scott B Geyer
(74) *Attorney, Agent, or Firm* — Studebaker & Brackett PC

(57) ABSTRACT

A method for manufacturing a gas sensor may be provided, the method comprising the steps of: preparing a porous base substrate; providing, on the porous base substarte, a source solution having graphene dispersed in a base solvent; manufacturing a graphene-impregnated base substrate by means of a driving process; and forming a first electrode and a second electrode on the graphene-impregnated base substrate.

4 Claims, 13 Drawing Sheets

(51) Int. Cl.
  *H01L 29/872* (2006.01)
  *G01N 27/404* (2006.01)
  *G01N 27/414* (2006.01)
  *G01N 27/407* (2006.01)
  *G01N 33/00* (2006.01)
  *B82Y 30/00* (2011.01)

(52) U.S. Cl.
  CPC ..... *G01N 27/4074* (2013.01); *G01N 27/4141* (2013.01); *G01N 33/005* (2013.01); *H01L 29/872* (2013.01); *B82Y 30/00* (2013.01)

(58) Field of Classification Search
  CPC ............ G01N 2291/021; G01N 33/005; H01L 29/1606; H01L 29/872; B82Y 30/00
  See application file for complete search history.

(56) References Cited

FOREIGN PATENT DOCUMENTS

| | | |
|---|---|---|
| KR | 10-2013-0032692 A | 4/2013 |
| KR | 10-2014-0070329 A | 6/2014 |
| KR | 10-2014-0106812 A | 9/2014 |
| KR | 10-2015-0017422 A | 2/2015 |
| KR | 10-1490023 B1 | 2/2015 |
| KR | 10-2015-0142744 A | 12/2015 |
| KR | 10-2016-0011722 A | 2/2016 |
| KR | 10-1671627 B1 | 11/2016 |

\* cited by examiner

FIG. 11A
FIG. 11B
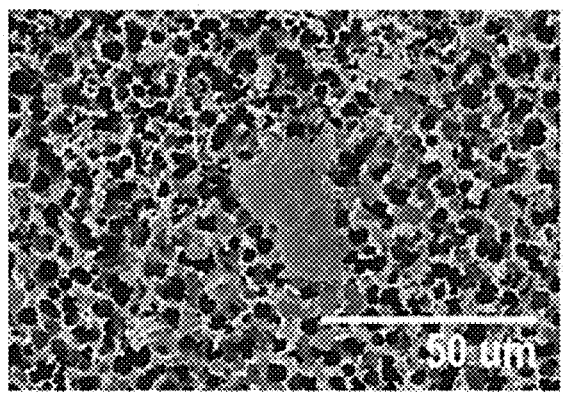
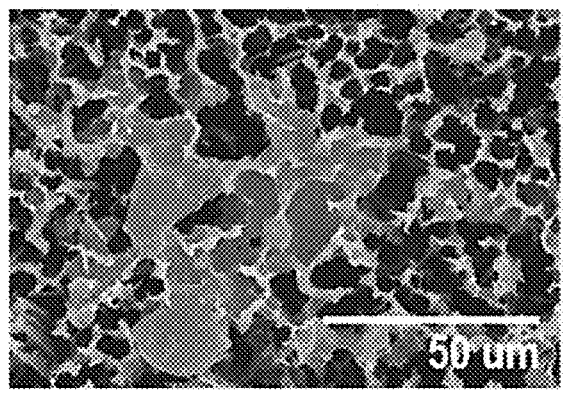
FIG. 12
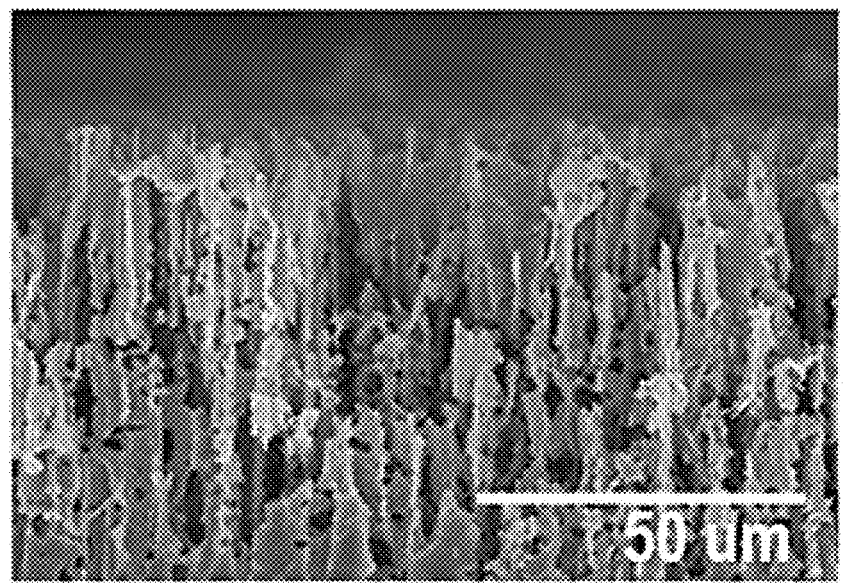

GAS SENSOR AND METHOD FOR MANUFACTURING SAME

CROSS-REFERENCE TO RELATED APPLICATIONS

The present application is a continuation of International Patent Application No. PCT/KR2018/002927, filed Mar. 13, 2018, which is based upon and claims the benefit of priority to Korean Patent Application No. 10-2017-0035844, filed on Mar. 22, 2017. The disclosures of the above-listed applications are hereby incorporated by reference herein in their entirety.

TECHNICAL FIELD

The present invention relates to a gas sensor and a method of manufacturing the same, and more particularly, to a gas sensor having excellent sensing characteristics using a graphene-supported base substrate manufactured by dropping and drying a source solution, in which graphene is dispersed, onto a porous base substrate, and a method of manufacturing the same.

BACKGROUND ART

Concerns about environmental pollution and depletion of fossil energy have raised interest in hydrogen energy as a low-pollution alternative energy source.

However, when being combined with oxygen in the atmosphere, hydrogen is spontaneously ignited or is exploded. Thus, a technology which can detect leakage of the hydrogen during production, storage, and use of the hydrogen is recognized as important.

Currently, hydrogen sensors, such as a semiconductor type hydrogen sensor, a field effect transistor (FET) type hydrogen sensor, an electrolytic type (electrochemical type) hydrogen sensor, an optical fiber type hydrogen sensor, a piezoelectric type hydrogen sensor, and a thermoelectric type hydrogen sensor, have been actively researched and developed.

In particular, in order to commercialize the hydrogen sensor, a measurement concentration range of the sensor, a short response time, precision, sensitivity, stability, miniaturization of the sensor, simplification of a process, and the like have been recognized as important.

For example, Korean Patent Application Publication No. KR20160011722A (Korean Patent Application No. KR20140092371A, Applicant: KAIST) discloses a technology of manufacturing a hydrogen sensor element, in which a housing including a gas separation membrane is combined with a sensor unit that can detect the concentration of hydrogen gas, liquid cannot pass through a sealed space in the housing, only dissolved hydrogen gas can pass through the gas separation membrane, and such a hydrogen sensor element is detachably coupled to an opening portion of a container in which liquid is accommodated, so that the concentration of the dissolved hydrogen gas can be measured using a simple method.

Currently, in order to commercialize the hydrogen sensor, researches on a technology of manufacturing a hydrogen sensor which has hydrogen-sensitive characteristics improved due to a simple and inexpensive process, and can easily perform measurement at the room temperature.

Technical Problem

A technical objective of the present invention is to provide a gas sensor which can perform measurement at the room temperature, and a method for manufacturing the same.

Another technical objective of the present invention is to provide a gas sensor having high-precision sensitivity and a method for manufacturing the same.

Yet another technical objective of the present invention is to provide a gas sensor having a wide measurement concentration range and a method for manufacturing the same.

Yet another technical objective of the present invention is to provide a gas sensor having excellent selectivity and a method for manufacturing the same.

Yet another technical objective of the present invention is to provide a gas sensor having reproducibility and a method for manufacturing the same.

Yet another technical objective of the present invention is to provide a gas sensor having long-term stability and a method for manufacturing the same.

Yet another technical objective of the present invention is to provide a gas sensor having reduced processing costs and a method for manufacturing the same.

Yet another technical objective of the present invention is to provide a gas sensor which can be miniaturized and a method for manufacturing the same.

Yet another technical objective of the present invention is to provide a gas sensor which is easily commercialized and a method for manufacturing the same.

The technical objectives of the present invention are not limited to the above description.

Technical Solution

In order to solve the above-described technical problems, the present invention provides a method of manufacturing a gas sensor.

According to one embodiment, the method of manufacturing a gas sensor may include: preparing a porous base substrate; providing a source solution, in which graphene is dispersed in a base solvent, onto the porous base substrate; manufacturing a graphene-supported base substrate through a drying process; and forming a first electrode and a second electrode on the graphene-supported base substrate.

According to the embodiment, the manufacturing of the graphene-supported base substrate may include supporting the graphene in a porous structure on a surface of the porous base substrate while reducing the base solvent contained in the source solution through the drying process.

According to the embodiment, the base solvent may include water or an organic solvent.

According to the embodiment, the providing of the source solution may include dropping the source solution onto the porous base substrate.

According to the embodiment, the concentration of the source solution may be more than 0 mg/mL and less than 10 mg/mL.

According to the embodiment, the porous base substrate may be manufactured through depositing a metal thin film on a base substrate, forming a nanoparticle including the metal on the base substrate through a thermal treatment process, and etching the base substrate using the nanoparticle.

According to the embodiment, the first electrode and the second electrode may be spaced apart from each other on an upper surface of the graphene-supported base substrate.

In order to solve the above-described technical problems, the present invention provides a gas sensor.

According to the embodiment, the gas sensor may include a porous base substrate, graphene supported in the porous structure on a surface of the porous base substrate, and first and second electrodes disposed on the porous base substrate.

According to the embodiment, the first and second electrodes may be spaced apart from each other on an upper surface of the graphene-supported porous base substrate.

According to the embodiment, the gas sensor may include adsorbing target gas to the graphene-supported base substrate, changing an electric conductivity value of the porous base substrate by reaction between the graphene and the target gas, and deriving a type and a concentration of the target gas by measuring a change in the electric conductivity value through the first and second electrodes.

According to the embodiment, a current and voltage curve (an IV curve) of the graphene-supported base substrate may form Schottky junction in a room temperature environment.

According to the embodiment, the porous structure has a form of a hole extending from an upper surface toward a lower surface of the porous base substrate.

Advantageous Effects

According to the embodiment of the present invention, a method of manufacturing a gas sensor having excellent sensitivity characteristics in a simplified process may be provided through a step of preparing the porous base substrate, a step of providing the source solution, in which the graphene is dispersed in the base solvent, onto the porous base substrate, a step of manufacturing the graphene-supported base substrate through a drying process, and a step of forming the first electrode and the second electrode on the graphene-supported base substrate.

First, the porous base substrate having a large specific surface area may be manufactured by using a simple and inexpensive process using electrochemical etching.

Further, the graphene-supported base substrate may be easily manufactured in a simple process of dropping the source solution, in which the graphene is dispersed, onto the manufactured porous base substrate, and then performing drying.

Accordingly, an expensive post-treatment process required for depositing a sensor material according to the related art on a substrate may be omitted, so that the process of manufacturing the gas sensor may be simplified, and process costs and a process time can be reduced.

Further, the graphene having a relatively large specific surface area is supported on the porous base substrate having a large specific surface area, so that the depletion layer generated in a heterojunction region of the porous base substrate and the graphene may be widely distributed.

Accordingly, the change in the electric conductivity of the porous base substrate due to reaction of the target gas and the graphene may be easily sensed.

In addition, the current and voltage curve (the IV curve) of the graphene-supported base substrate may form Schottky junction in the room temperature environment.

Thus, according to the embodiment of the present invention, the method of manufacturing a gas sensor having excellent responsiveness to the target gas at the room temperature environment may be provided.

Further, the size and/or the amount of the graphene supported on the porous base substrate may be easily adjusted in a simple method of adjusting the concentration and/or the amount of the source solution provided to the porous base substrate.

Accordingly, the optimum amount of the graphene having an optimum size, which is suitable for the type and/or the sensing concentration range of the target gas, is supported on the porous base substrate, so that the gas sensor having excellent sensing characteristics may be provided.

BRIEF DESCRIPTION OF DRAWINGS

FIGS. 11A to 11B are SEM images of base substrates in which graphene is supported according to the concentration of a source solution according to fifth and sixth embodiments of the present invention;

FIG. 12 is a lateral SEM image of the graphene-supported base substrate according to the sixth embodiment of the present invention;

DETAILED DESCRIPTION

Figure 1:
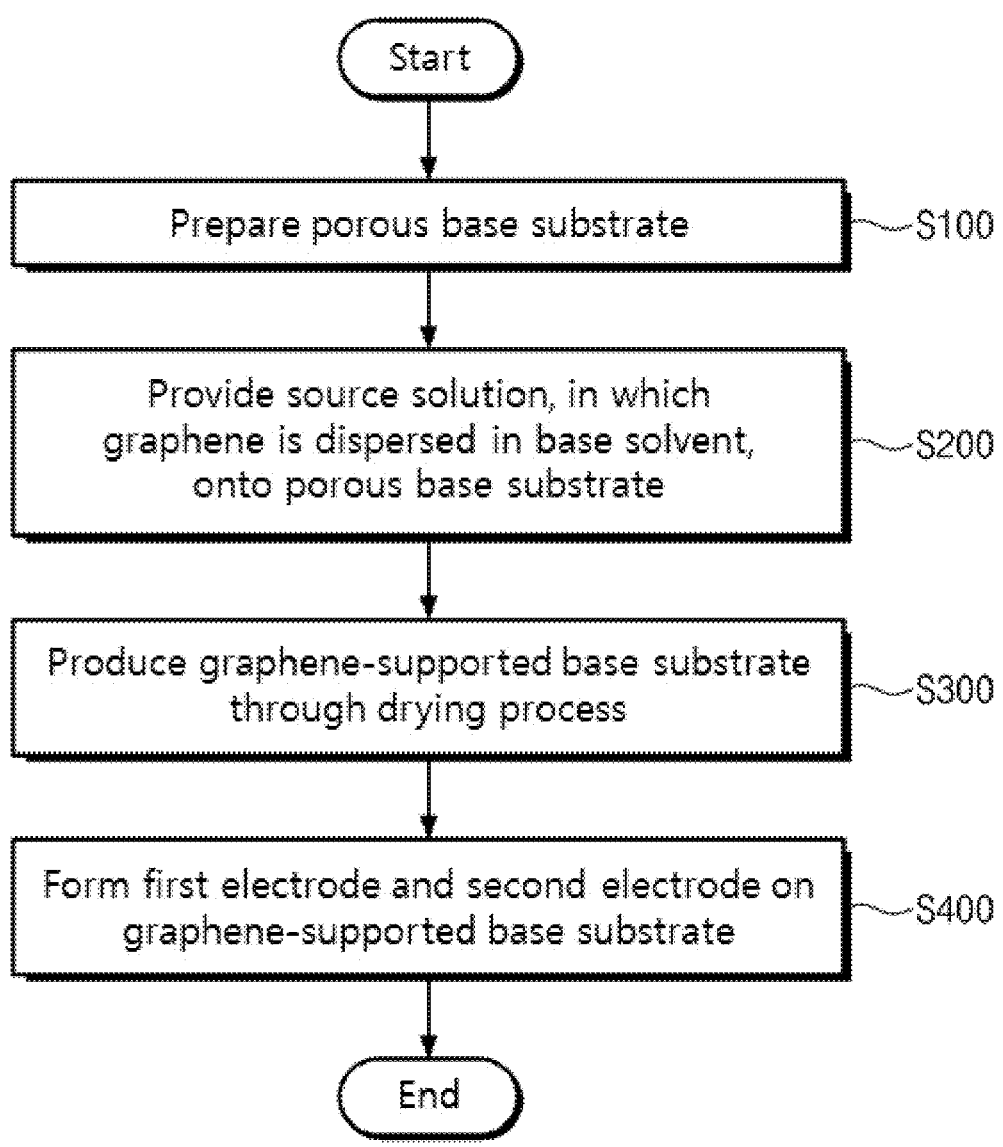
FIG. 1 is a flowchart illustrating a method for manufacturing a gas sensor according to an embodiment of the present invention.

Hereinafter, exemplary embodiments of the present invention will be described in detail with reference to the accompanying drawings.

However, the technical spirit of the present invention is not limited to embodiments described herein but may be embodied in other forms.

Instead, the embodiments described herein are provided such that contents disclosed can be thorough and complete and the spirit of the present invention can be fully transferred to those skilled in the art.

In the present specification, in a case where it is mentioned that a first component is located on a second component, this case means that the first component is directly formed on the second component or the first component is formed on the second component with a third component interposed therebetween.

Further, in the drawings, the thicknesses of films and regions are exaggeratedly illustrated for effective description of the technical contents.

Further, although terms "first", "second", "third", and the like in various embodiments of the present specification are used to describe various components, these components should not be limited by these terms.

These terms have only been used to distinguish one component from another component.

Thus, a component, which is mentioned as a first component in any one embodiment, may be mentioned as a second component in another embodiment.

The embodiments described and exemplified herein include a complementary embodiment therefor.

Further, in the present specification, the term "and/or" is used to mean that a component includes at least one of components listed before and after the term.

in the specification, a singular expression includes a plural expression unless the context is clearly stated otherwise.

Further, the term "include" or "have" is intended to specify presence of features, numbers, steps, components, and combinations thereof stated in the specification, but should not be understood to exclude presence or addition of one or more other features, numbers, steps, components, and combinations thereof.

Further, in the following description of the present invention, when it is determined that detailed description of related widely-known functions or configurations makes the subject matter of the present invention unclear, the detailed description will be omitted.

Figure 2:
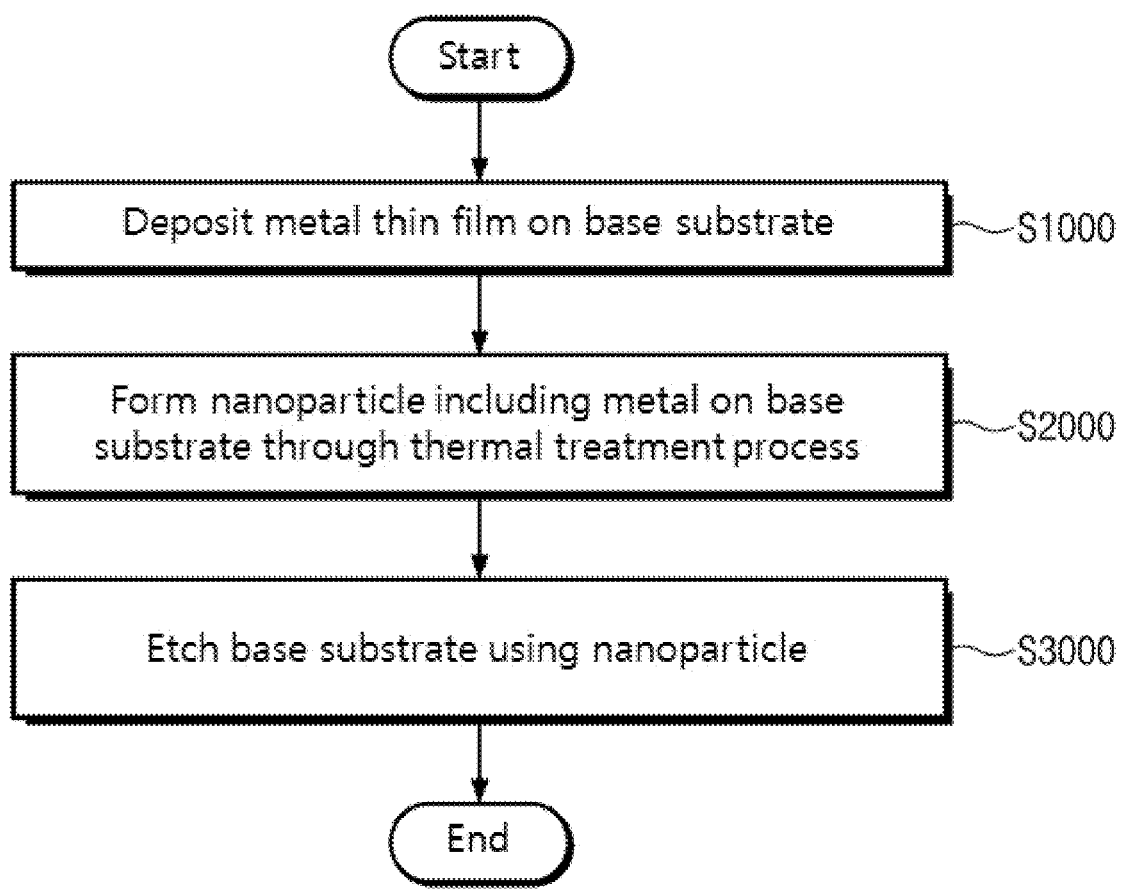
FIG. 2 is a flowchart illustrating a method for manufacturing a porous base substrate according to the embodiment of the present invention.
Figure 3:
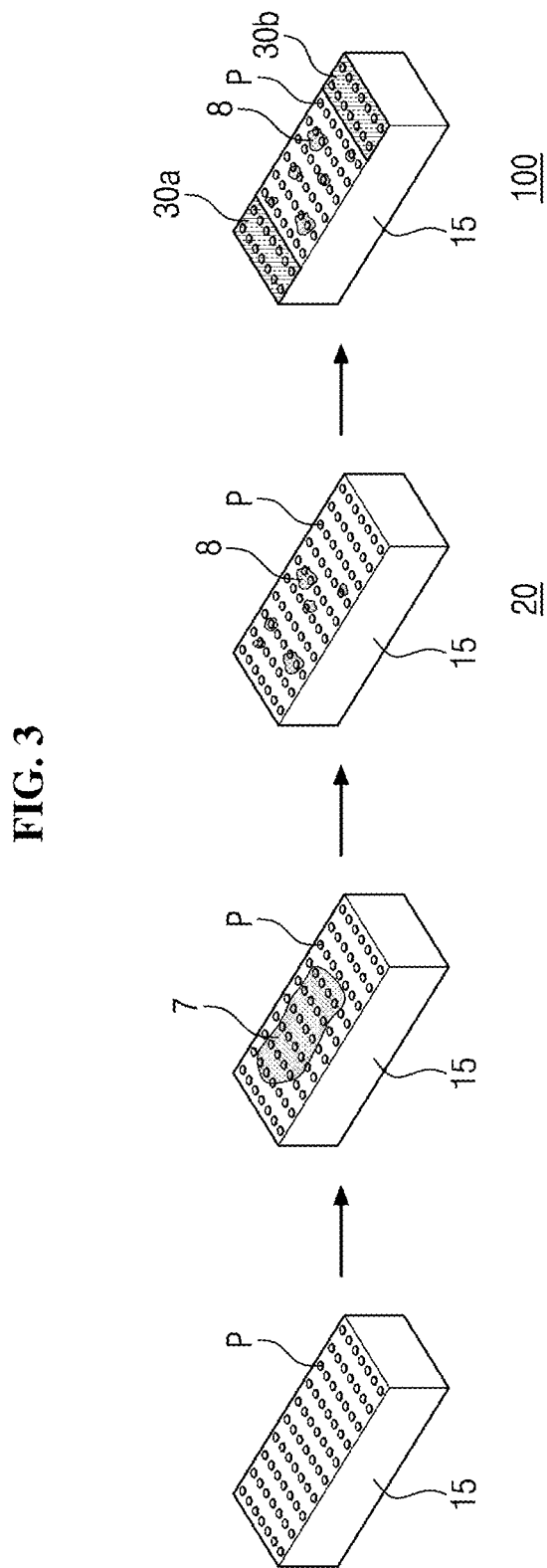
FIG. 3 is a diagram illustrating the method for manufacturing a gas sensor according to the embodiment of the present invention.
Figure 4:
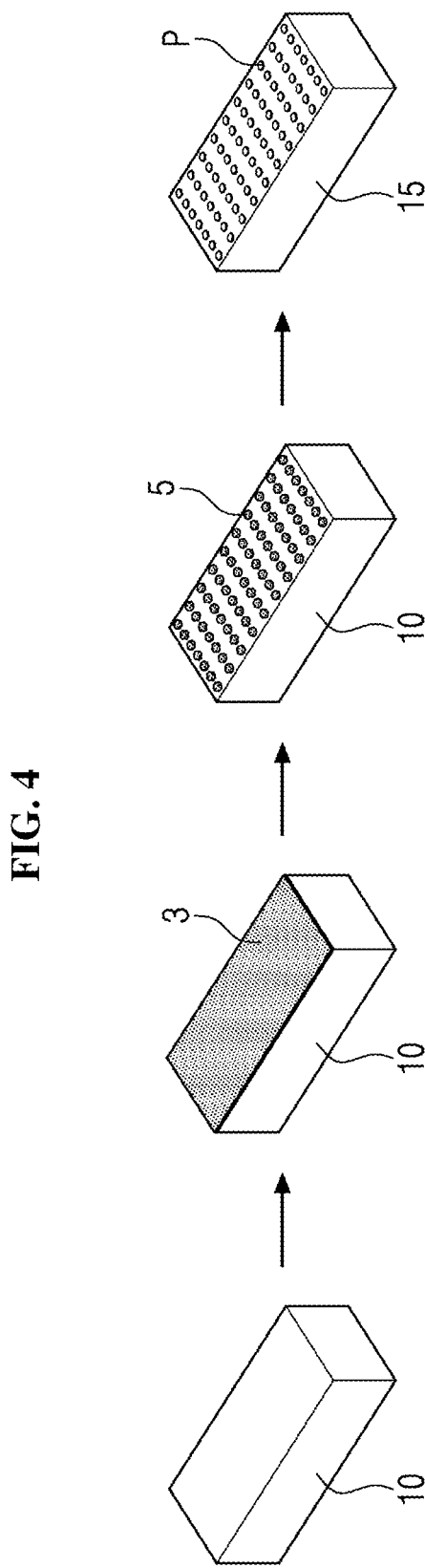
FIG. 4 is a diagram illustrating the method for manufacturing a porous base substrate according to the embodiment of the present invention.
Figure 5:
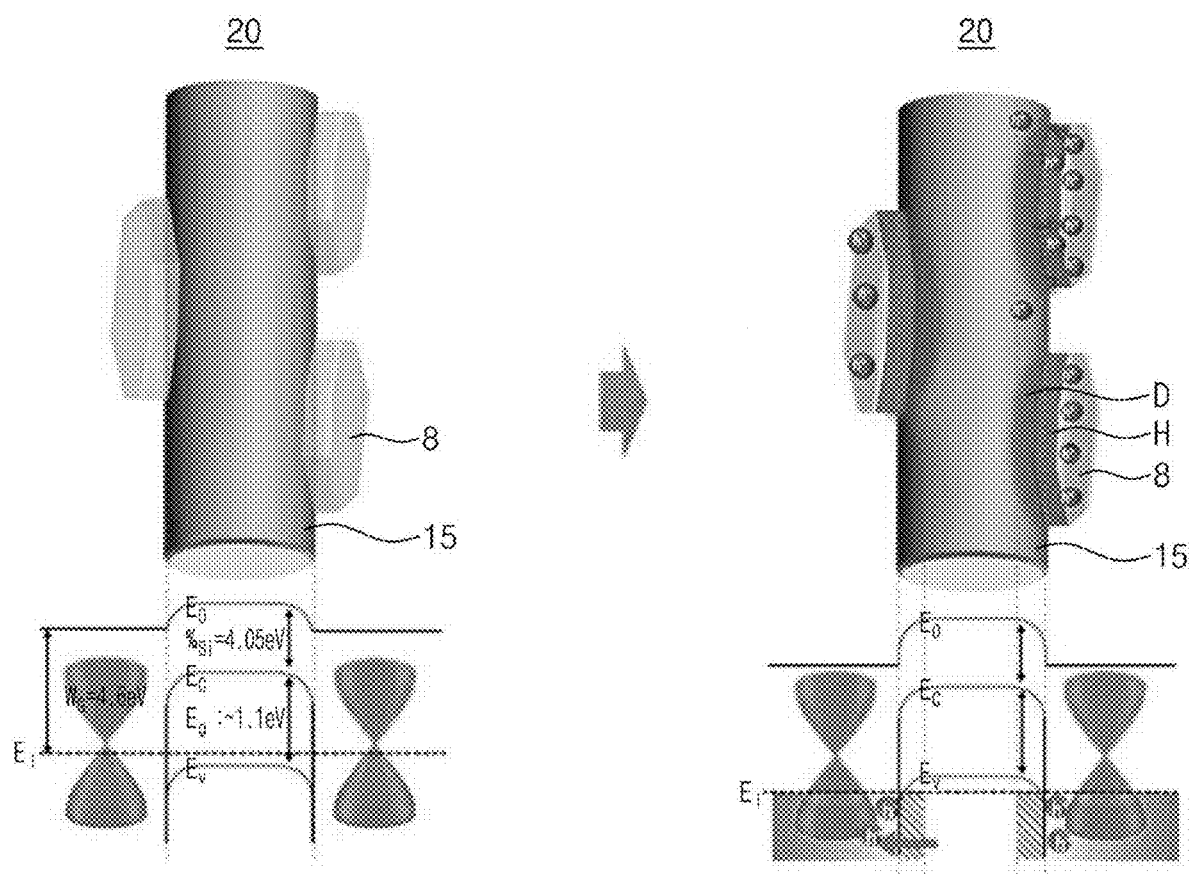
FIGS. 5 and 6 are schematic diagrams illustrating a mechanism of sensing hydrogen ($H_2$) gas by the gas sensor according to the embodiment of the present invention.
Figure 6:
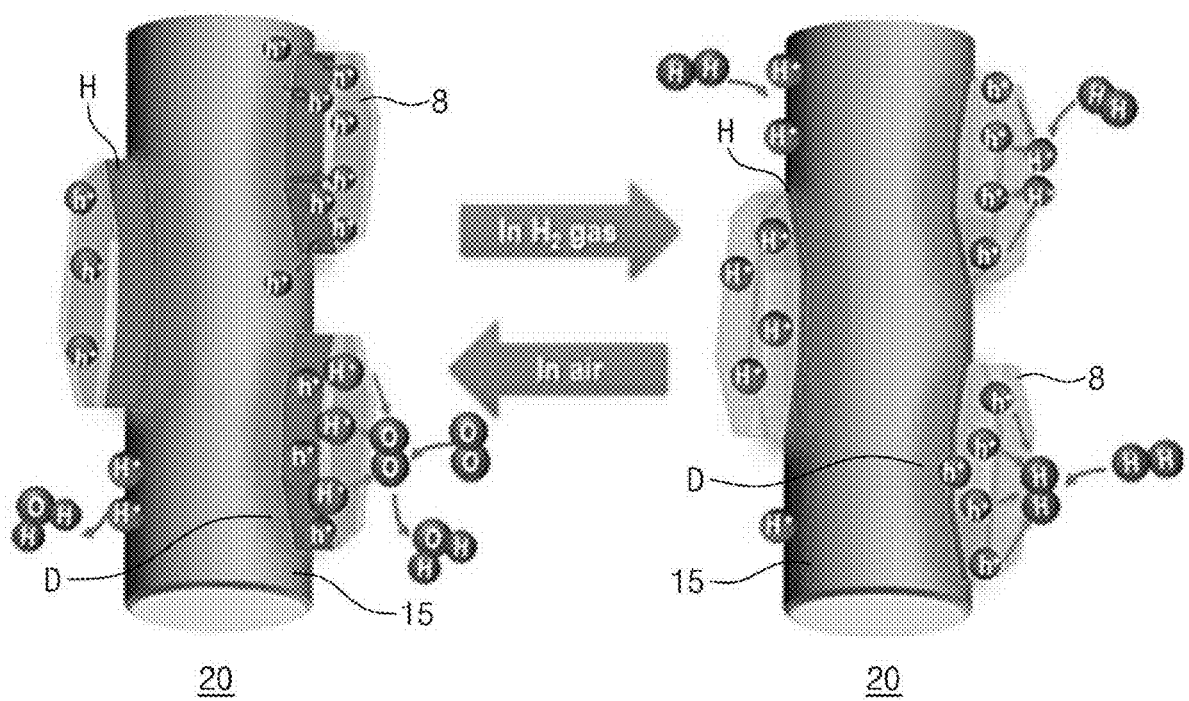

FIG. 1 is a flowchart illustrating a method for manufacturing a gas sensor according to an embodiment of the present invention, FIG. 2 is a flowchart illustrating a method for manufacturing a porous base substrate according to the embodiment of the present invention, FIG. 3 is a diagram illustrating the method for manufacturing a gas sensor according to the embodiment of the present invention, FIG. 4 is a diagram illustrating the method for manufacturing a porous base substrate according to the embodiment of the present invention, and FIGS. 5 and 6 are schematic diagrams illustrating a mechanism of sensing hydrogen ($H_2$) gas by the gas sensor according to the embodiment of the present invention.

Referring to FIGS. 1 to 6, a porous base substrate 15 may be prepared (S100).

As illustrated in FIGS. 2 and 4, the porous base substrate 15 may be prepared through a step of depositing a metal thin film 3 on a base substrate (S1000), a step of forming a nanoparticle 5 including the meal on the base substrate 10 (S2000), and a step of etching the base substrate 10.

First, the metal thin film 3 may be deposited on the base substrate 10 (S1000).

According to the embodiment, the metal thin film 3 may be deposited on the base substrate 10 by an E-beam evaporation method.

According to the embodiment, the base substrate 10 may include p-type silicon, and the metal thin film 3 may include platinum (Pt).

The nanoparticle 5 including the metal may be formed on the base substrate 10 through a thermal treatment process (S2000).

According to the embodiment, a platinum (Pt) nanoparticle may be formed on the p-type silicon substrate by the thermal treatment process.

According to the embodiment, the thermal treatment process at a temperature of 650□ may be performed on the base substrate 10 on which the metal thin film 3 is deposited.

The base substrate 10 may be etched using the nanoparticle 5 (S3000).

In other words, the porous base substrate 15 having a porous structure P may be manufactured by the etching process using the nanoparticle 5.

According to the embodiment, the base substrate 10 may be electrochemically etched by an anodizing process.

In detail, after the base substrate 10 in which the nanoparticle 5 is formed is supported in an electrolyte, a current is applied in a state in which the nanoparticle 5 and the base substrate 10 are used as a cathode and an anode, respectively, so that the porous base substrate 15 may be manufactured.

According to the embodiment, the porous structure P may have the form of a hole extending from the upper surface toward the lower surface of the porous base substrate 15.

According to the embodiment, the diameter of the hole may be several μm.

According to the embodiment, after the p-type silicon substrate on which the platinum (Pt) nanoparticle is formed is supported in an electrolyte containing hydrofluoric acid (HF) and hydrogen peroxide ($H_2O_2$), a current of 10 mA/cm$^2$ is applied in a state in which the platinum (Pt) nanoparticle and the p-type silicon substrate are used as the cathode and the anode, respectively, so that a porous p-type silicon substrate may be manufactured.

According to the embodiment, the step of preparing the porous base substrate 15 may further include a step of washing the base substrate 10 before the step of depositing the metal thin film 3 on the base substrate 10 (S1000).

The step of washing the base substrate 10 may further include a step of removing impurities, a step of removing organic matters, and a step of removing a naturally oxidized layer (patina).

According to the embodiment, the step of removing impurities may include removing impurities existing on the p-type silicon substrate by acetone and distilled water.

According to the embodiment, the step of removing organic matters may include removing organic matters remaining on the p-type silicon substrate by supporting the p-type silicon substrate in a solution in which sulfuric acid ($H_2SO_4$), hydrogen peroxide ($H_2O_2$), and distilled water are mixed with each other at a ratio of 6:3:1, for 10 minutes at a temperature of 80 □.

According to the embodiment, the step of removing the naturally oxidized layer may include removing a naturally oxidized layer existing on the surface of the p-type silicon substrate by supporting the p-type silicon substrate in a solution containing 10 wt % of hydrofluoric (HF) acid for 10 minutes at the room temperature environment.

According to the embodiment, the step of washing the base substrate 10 may further include a step of washing the p-type silicon substrate using distilled water after the step of removing the naturally oxidized layer is terminated.

Continuously, referring to FIGS. 1 and 3, a source solution 7 in which graphene 8 is dispersed in a base solvent may be provided onto the porous base substrate 15.

In detail, the source solution 7 is dropped onto the porous base substrate 15, so that the source solution 7 may be provided to the surface of the porous base substrate 15 and the porous structure P.

According to the embodiment, the source solution 7 may be micro-pipet-dropped on the porous base substrate 15.

According to the embodiment, the amount and/or the size of the graphene 8 supported in the porous structure P may be adjusted according to the amount of the source solution 7 provided to the porous base substrate 15.

According to the embodiment, as the amount of the source solution 7 provided onto the porous base substrate 15 increases, the graphene 8 is agglomerated. Thus, the graphene 8 having a diameter of several μm to several tens of μm may be supported in the porous structure P.

Further, according to the embodiment, the sensing sensitivity of the gas sensor 100 according to the embodiment of the present invention may be adjusted according to the concentration of the source solution 7 provided onto the porous base substrate 15.

According to the embodiment, a method of manufacturing the gas sensor 100 having excellent sensing sensitivity according to the embodiment of the present invention when the concentration of the graphene 8 supported in the porous structure P in the source solution 7 is more than 0 mg/mL and less than 10 mg/mL may be provided.

According to the embodiment, the source solution 7 may be produced by dispersing the graphene 8 in the base solvent.

According to the embodiment, the base solvent may be water.

Accordingly, a process of manufacturing the gas sensor 100 according to the embodiment of the present invention may be an environment-friendly process.

According to another embodiment, the base solvent may be an organic solvent.

When the organic solvent is used as the base solvent, oxidation reaction occurring in an edge of the graphene 8 is minimized, so that the gas sensor 100 having high sensitivity characteristics may be manufactured.

For example, the organic solvent may be ethanol, Di-Methyl Formamide (DMF), or N-Methylpyrrolidone (NMP).

A base substrate 20 in which graphene is supported may be manufactured through a drying process (S300).

In other words, while the base solvent contained in the source solution 7 is removed through the drying process, the graphene 8 may be supported in the porous structure P on the porous base substrate 15.

According to the embodiment, the graphene 8 may be supported in the porous structure P of the porous base substrate 15 in a depth of several μm to several tens of μm.

According to the embodiment, the graphene 8 may be supported on the porous structure P of the porous base substrate 15 and on the surface of the porous base substrate 15 in which the porous structure P is not formed.

A heterostructure may be formed between the graphene 8 and the porous base substrate 15 on the surface of the porous base substrate 15 including the porous structure P.

Accordingly, a method of manufacturing the gas sensor 100 having improved sensing efficiency may be provided.

According to the embodiment, a current and voltage curve (an IV curve) of the graphene-supported base substrate 20 may form Schottky junction in the room temperature environment.

Accordingly, a threshold voltage (Vth) of the gas sensor 100 relatively decreases, and power efficiency of a circuit increases, so that signal distortion of the gas sensor 100 may be minimized.

Accordingly, according to the embodiment of the present invention, a method of manufacturing the gas sensor 100 having excellent sensing ability at the room temperature and improved sensing measurement efficiency may be provided.

According to the embodiment, the porous base substrate 15 to which the source solution 7 is provided is dried for 20 minutes at a temperature environment of 100 □ in the atmosphere. Thus, while the base solvent and/or remaining water contained in the source solution 7 are removed, the graphene-supported base substrate 20 may be manufactured.

A first electrode 30a and a second electrode 30b may be formed on the graphene-supported base substrate 20 (S400).

In detail, the first electrode 30a and the second electrode 30b are spaced apart from each other on the upper surface of the graphene-supported base substrate 20, so that the gas sensor 100 according to the embodiment of the present invention may be manufactured.

According to the embodiment, gold (Au) electrodes may be spaced apart from each other on the upper surface of the graphene-supported base substrate 20 by the E-beam evaporation method.

As described above, the gas sensor 100 according to the embodiment of the present invention, manufactured using the graphene-supported base substrate 20, may derive the type and the concentration of the target gas through a step of adsorbing a target gas, a step of changing the electric conductivity value of the porous base substrate 15, and a step of measuring a change in the electric conductivity value.

The step of adsorbing the target gas may include reacting the target gas with the graphene 8 of the graphene-supported base substrate 20.

As illustrated in FIGS. 5 and 6, when the graphene 8 is supported and bonded to the porous base substrate 15, holes of the porous base substrate 15 are moved to the graphene 8. Thus, a depletion layer D may be generated at a portion where the graphene 8 and the porous base substrate 15 are bonded to each other and a hole accumulation layer H may be formed in the graphene 8.

The target gas adsorbed to the graphene-supported base substrate 20 may be ionized to deprive holes accumulated in the graphene 8 so as to be adsorbed to the surface of the graphene 8.

The step of changing the electric conductivity value of the porous base substrate 15 may include changing the electric conductivity value of the porous base substrate 15 due to a decrease in the carrier density of the graphene 8.

In detail, the carrier density of the graphene 8, which is deprived of holes by the target gas, may be reduced.

Accordingly, the electric conductivity of the porous base substrate 15 in which the graphene 8 is supported may be reduced.

The step of measuring the change in the electric conductivity value may include deriving the type and the concentration of the target gas through the change in the electric conductivity value of the graphene-supported base substrate 20.

In the gas sensor 100 according to the embodiment of the present invention, since the graphene 8 having a large specific surface area is supported on the porous base substrate 15, distribution of the generated depletion layer D may be wide.

Accordingly, reaction to the above-described sensing mechanism for the target gas is easy, so that the gas sensor 100 having excellent sensitivity characteristics with respect to the target gas may be provided.

Hereinafter, a gas sensor according to the embodiment of the present invention will be described.

In description of the gas sensor according to the embodiment of the present invention, a portion overlapping the description of the method of manufacturing a gas sensor according to the embodiment of the present invention, illustrated in FIGS. 1 to 6, will be described with reference to FIGS. 1 to 6.

Referring to FIG. 3, the gas sensor according to the embodiment of the present invention may include the porous base substrate 15, the graphene 8, the first electrode 30*a*, and the second electrode 30*b*.

In the porous base substrate 15, as described with reference to FIGS. 1 to 6, the porous structure P may be formed on the surface of the base substrate 10.

According to the embodiment, the hole extending from the upper surface toward the lower surface of the porous base substrate 15 may be formed.

According to the embodiment, the diameter of the hole may be several μm.

As described with reference to FIGS. 2 and 4, the porous base substrate 16 may be manufactured through the step of depositing the metal thin plate 3 on the base substrate 10 (S1000), the step of forming the nanoparticle 5 including the metal on the base substrate 10 (S2000), and the step of etching the base substrate 10.

According to the embodiment, the platinum (Pt) thin film may be manufactured on the p-type silicon substrate by the E-beam evaporation method.

The p-type silicon substrate on which the platinum (Pt) thin film is deposited is thermally treated at a temperature of 650 □, so that the p-type silicon substrate in which a platinum nanoparticle is formed may be manufactured.

Thereafter, the porous p-type silicon substrate may be manufactured through an electrochemical etching process using the platinum (Pt) nanoparticle.

The graphene 8 may be supported on the surface of the porous base substrate 15 and/or on the porous structure P.

In detail, the graphene 8 may be supported on the porous structure P of the porous base substrate 15 and on the surface of the porous base substrate 15 in which the porous structure P is not formed.

According to the embodiment, the graphene 8 having a diameter of several μm to several tens of μm may be supported in the porous structure P.

Further, according to the embodiment, the graphene 8 may be supported in the porous structure P of the porous base substrate 15 in a depth of several μm to several tens of μm.

According to the embodiment, a current and voltage curve (an IV curve) of the graphene-supported base substrate 20 may form Schottky junction in the room temperature environment.

Accordingly, according to the embodiment of the present invention, the gas sensor 100 having excellent room-temperature sensing ability may be provided.

According to the embodiment, the source solution 7 in which the graphene 8 is dispersed in water or an organic solvent may be micro-pipet-dropped on the porous base substrate 15.

The porous base substrate 15 to which the source solution 7 is provided is dried for 20 minutes in a temperature environment of 100 □ in the atmosphere, so that the graphene-supported base substrate 20 may be manufactured.

The first and second electrodes 30*a* and 30*b* may be disposed on the porous base substrate 15.

In detail, the first and second electrodes 30*a* and 30*b* may be spaced apart from each other on the upper surface of the graphene-supported base substrate 20.

According to the embodiment, gold (Au) electrodes may be spaced apart from each other on the upper surface of the graphene-supported base substrate 20 by the E-beam evaporation method.

As described above, the gas sensor 100 according to the embodiment of the present invention may derive the type and the concentration of the target gas through the step of adsorbing the target gas, the step of changing the electric conductivity value of the porous base substrate 15, and the step of measuring the change in the electric conductivity.

As described with reference to FIGS. 5 and 6, the target gas adsorbed to the graphene-supported base substrate 20 may deprive the holes accumulated in the graphene 8 to be ionized so as to be adsorbed on the surface of the graphene 8.

The electric conductivity value of the porous base substrate 15 may be reduced due to a decrease in the carrier density of the graphene 8.

The type and the concentration of the target gas may be derived through the change in the electric conductivity value of the graphene-supported base substrate 20.

As described above, in the gas sensor 100 according to the embodiment of the present invention, since the graphene 8 having a large specific surface area is widely supported on the porous base substrate 15, the above-described sensing mechanism response to the target gas may be easy.

Accordingly, the gas sensor 100 having excellent sensitivity to the target gas may be provided.

Unlike the above-described embodiments of the present invention, a metal oxide semiconductor-type gas sensor and a graphene-based gas sensor are used in order to sense explosive gas and toxic gas such as hydrogen ($H_2$), nitrogen dioxide ($NO_2$), hydrogen sulfide ($H_2S$), and ammonia ($NH_3$), and oxygen ($O_2$) gas for environmental control.

First, the metal oxide semiconductor-type gas sensor has been most widely used because of high sensitivity, a rapid response speed, and the like, but has disadvantages in that the metal oxide semiconductor-type gas sensor has low in gas selectivity and is limited in operation in extreme environments such as humidity and strong acidity.

Further, since power consumption is high due to a high driving temperature of several hundreds of degrees Celsius, and an additional heat source should be attached to the inside of the sensor to drive the sensor, there is a limit to miniaturization of the sensor.

Further, the graphene-based gas sensor has an advantage in that an operating temperature is low. However, since not pure graphene but metal-added graphene or a metal oxide-graphene mixed material is used, there is a disadvantage in that when deposition is performed on a substrate after a sensor material is synthesized, complicated processes including the thermal treatment process and expensive post-treatment processes such as an ink jet printer are required.

A silicon substrate-based graphene gas sensor for solving these problems may be manufactured by arranging and hetero-joining the graphene to the upper end of a silicon nanowire used as a substrate.

However, there is a problem in that application is limited only to a uniformly generated nanowire substrate, and a graphene-silicon hetero junction area is limited.

As described above, according to the embodiment of the present invention, the method of manufacturing the gas sensor 100 having excellent sensitivity characteristics in a simplified process may be provided through a step of preparing the porous base substrate 15, a step of providing the source solution 7, in which the graphene 8 is dispersed in the base solvent, onto the porous base substrate 15, a step of manufacturing the graphene-supported base substrate 20 through a drying process, and a step of forming the first electrode 30a and the second electrode 30b on the graphene-supported base substrate 20.

First, the porous base substrate 15 having a large specific surface area may be manufactured by using a simple and inexpensive process using electrochemical etching.

Further, the graphene-supported base substrate 20 may be easily manufactured in a simple process of dropping the source solution 7, in which the graphene 8 is dispersed, onto the manufactured porous base substrate 15, and then performing drying.

Accordingly, an expensive post-treatment process required for depositing a sensor material according to the related art on a substrate may be omitted, so that the process of manufacturing the gas sensor 100 may be simplified, and process costs and a process time can be reduced.

Further, the graphene 8 having a relatively large specific surface area is supported on the porous base substrate 15 having a large specific surface area, so that the depletion layer D generated in a heterojunction region of the porous base substrate 15 and the graphene 8 may be widely distributed.

Accordingly, the change in the electric conductivity of the porous base substrate 15 due to reaction of the target gas and the graphene 8 may be easily sensed.

In addition, the current and voltage curve (the IV curve) of the graphene-supported base substrate 20 may form Schottky junction in the room temperature environment.

Thus, according to the embodiment of the present invention, a method of manufacturing the gas sensor 100 having excellent responsiveness to the target gas at the room temperature environment may be provided.

Further, the size and/or the amount of the graphene 8 supported on the porous base substrate 15 may be easily adjusted in a simple method of adjusting the concentration and/or the amount of the source solution 7 provided to the porous base substrate 15.

Accordingly, the optimum amount of the graphene 8 having an optimum size, which is suitable for the type and/or the sensing concentration range of the target gas, is supported on the porous base substrate 15, so that the gas sensor 100 having excellent sensing characteristics may be provided.

Hereinafter, characteristic evaluation of the gas sensor manufactured according to the embodiment of the present invention will be described.

Method of Manufacturing Gas Sensor According to Embodiments

After impurities existing on the p-type silicon substrate are washed using acetone and distilled water, the p-type silicon substrate is immersed for 10 minutes in an environment of 80 □ in a solution in which sulfuric acid ($H_2SO_4$), hydrogen peroxide ($H_2O_2$), and distilled water are mixed with each other in a ratio of 6:3:1, so that organic matters existing on the p-type silicon substrate are removed.

The p-type silicon substrate is immersed in a solution having 10 wt % of hydrofluoric acid for 10 minutes at the room temperature environment, so that the naturally oxidized layer on the surface of the p-type silicon substrate is removed. Thereafter, the p-type silicon substrate is washed with distilled water.

After the platinum (Pt) thin film is deposited on the p-type silicon substrate using the E-beam evaporation method, the thermal treatment process is performed in a temperature environment of 650 □, so that the platinum (Pt) nanoparticle is formed on the p-type silicon substrate.

The electrochemical etching process is performed using the platinum (Pt) nanoparticle as an anode and the p-type silicon substrate as a cathode in an electrolyte containing hydrofluoric acid (HF) and hydrogen peroxide ($H_2O_2$), so that the porous silicon substrate is manufactured.

While the amount (10 µl, 30 µl, 50 µl, and 100 µl) of the source solution having a concentration of 0.1 mg/mL, in which the graphene is dispersed in ethanol, is changed, the source solution is provided onto the porous silicon substrate through a micro pipet.

Thereafter, the thermal treatment process is performed for 20 minutes at a temperature of 100 □ in the atmosphere to remove the ethanol and residual moisture contained in the source solution, so that the graphene-supported p-type silicon substrate is manufactured.

The gold thin films are deposited on the upper surface of the graphene-supported P-type silicon substrate through the E-beam evaporation method, to be spaced apart from each other. Thus, the first and second electrodes are formed on the graphene-supported P-type silicon substrate, so that gas sensors according to first to fourth embodiments of the present invention are manufactured.

Further, although the same method of manufacturing the gas sensors according to the embodiments is used, 100 µl of the source solutions having different concentrations (0.1 mg/mL and 1 mg/mL) are provided onto the porous silicon substrate, so that gas sensors according to fifth and sixth embodiments of the present invention are manufactured.

In addition, the source solutions having different concentrations and different amounts of the graphene (0.1 mg/mL (0.01 mg), 1 mg/mL (0.1 mg), and 10 mg/mL (1 mg)) are provided onto the porous base substrate, so that gas sensors according to seventh to ninth embodiments of the present invention are manufactured.

Method of Manufacturing Gas Sensor According to Comparative Example

Although the same method of manufacturing the gas sensors according to the embodiments is used, the step of providing the source solution onto the porous base substrate is omitted, and the porous base substrate in which the graphene is not supported is used, so that a gas sensor according to a comparative example for the embodiments of the present invention is manufactured.

Figure 7:
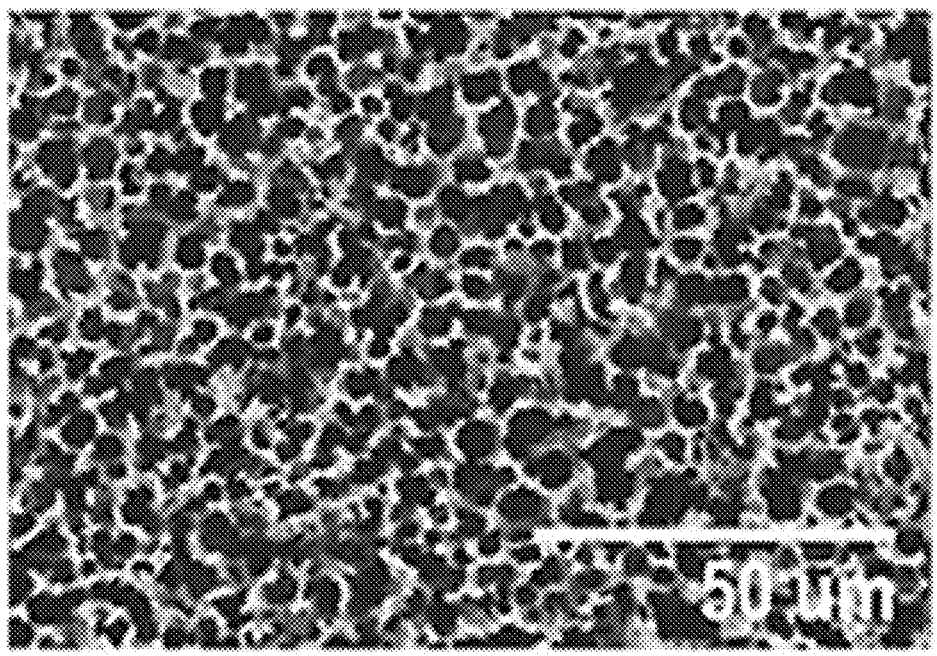
FIG. 7 is an SEM image of the porous base substrate according to the embodiment of the present invention.
Figure 8A:
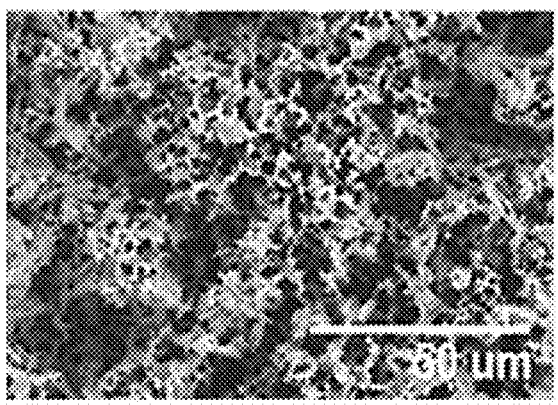
FIGS. 8A to 8D are SEM images of base substrates in which graphene is supported according to the amount of a source solution according to first to fourth embodiments of the present invention.
Figure 8B:
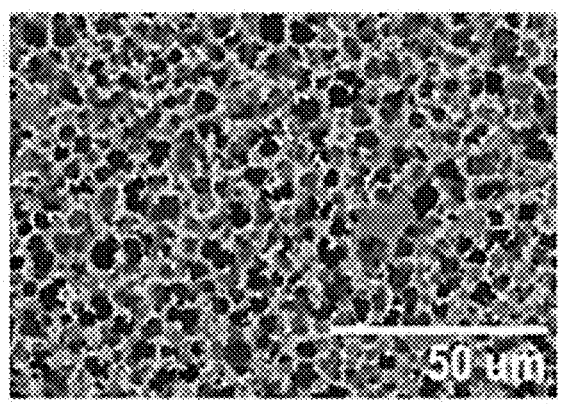
Figure 8C:
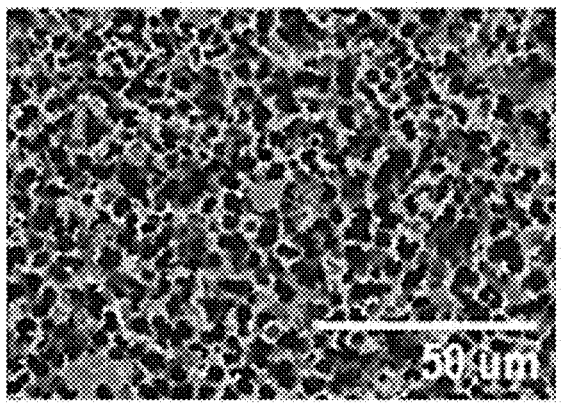
Figure 8D:
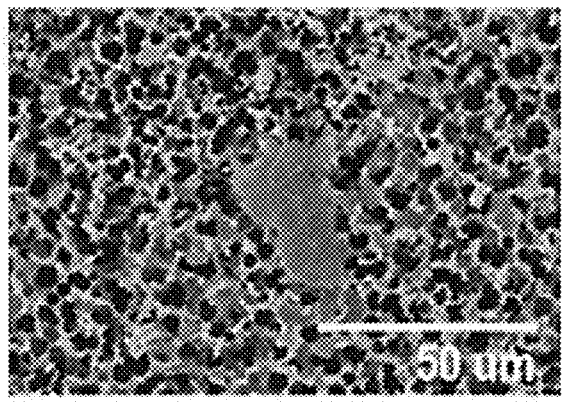

FIG. 7 is an SEM image of the porous base substrate according to the embodiment of the present invention.

The porous base substrate is manufactured according to the method of manufacturing the gas sensors according to the embodiments.

the surface shape of the porous base substrate according to the embodiment of the present invention is identified using a scanning electron microscope (SEM) apparatus.

Referring to FIG. 7, it is identified that a porous structure having a diameter of several μm is formed on the p-type silicon substrate through the electrochemical etching process using the platinum (Pt) nanoparticle.

FIGS. 8A to 8D are SEM images of base substrates in which graphene is supported according to the amount of a source solution according to first to fourth embodiments of the present invention.

In detail, FIGS. 8A, 8B, 8C, and 8D are SEM images of the graphene-supported base substrates according to the first to fourth embodiments of the present invention when different amounts (10 μl, 30 μl, 50 μl, and 100 μl) of the source solutions are provided onto the porous base substrate.

Referring to FIGS. 8A, 8B, 8C, and 8D, it is identified that the porous structure having a diameter of several μm is formed on the p-type silicon substrate.

Further, it is identified that as the amounts (10 μl, 30 μl, 50 μl, and 100 μl) of the source solutions provided onto the porous base substrate increases, the graphene having a size of several μm to several tens of μm is supported in the porous structure having a diameter of several μm on the p-type silicon substrate.

Further, it is identified that as the amounts (10 μl, 30 μl, 50 μl, and 100 μl) of the source solutions provided onto the porous base substrate increase, the graphene having a size of several μm to several tens of μm is supported in the porous structure having a diameter of several μm on the p-type silicon substrate.

From this, it can be identified that the amount of the graphene that is a sensing substance supported in the porous structure formed on the porous base substrate may be easily controlled in a simple method of adjusting the amount of the source solution provided onto the porous base substrate.

Figure 9:
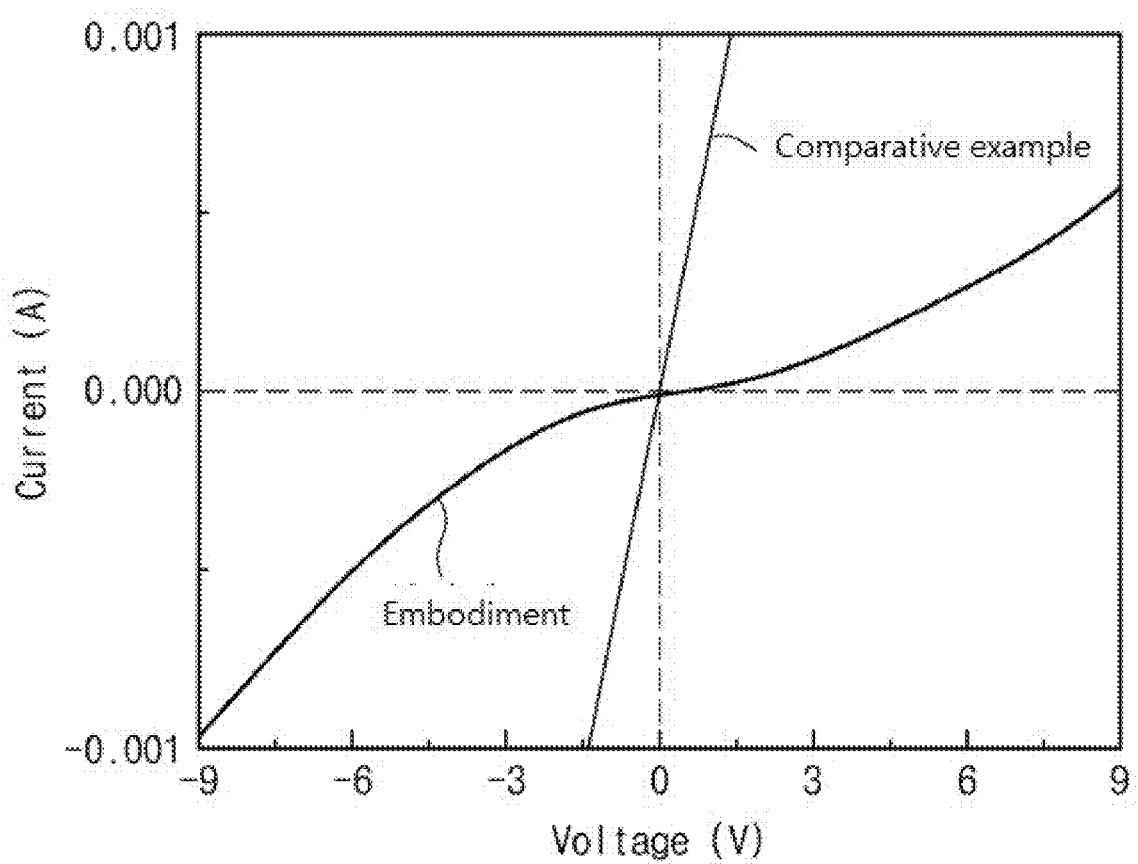
FIG. 9 is a graph depicting current and voltage curves (IV curves) of gas sensors according to the embodiment of the present invention and a comparative example for the embodiment.

FIG. 9 is a graph depicting current and voltage curves (IV curves) of gas sensors according to the embodiment of the present invention and a comparative example for the embodiment.

A current I according to a voltage V is measured with respect to the gas sensor manufactured using the graphene-supported base substrate according to the method of manufacturing a gas sensor according to the embodiments and the gas sensor manufactured using the porous base substrate in which the graphene is not supported according to the method of manufacturing a gas sensor according to the comparative example.

Referring to FIG. 9, it is identified that the IV curve of the gas sensor according to the comparative example for the embodiment of the present invention, which is manufactured using the porous base substrate in which the graphene is not supported, shows Ohmic contact at the room temperature environment.

On the other hand, a Schottky barrier between the graphene and the porous base substrate is formed due to the graphene-supported base substrate and a heterostructure of the graphene showing metal characteristics, so that some of carriers in the porous base substrate may be moved to the graphene.

As a result, the energy level of the graphene-supported base substrate is lowered, so that the depletion layer and an electric field may be formed between the graphene and the porous base substrate.

Accordingly, it is identified that the IV curve of the gas sensor according to the embodiment of the present invention, which is manufactured using the graphene-supported base substrate, shows Schottky junction in the room temperature environment.

Based on the result of FIG. 9, in the gas sensor according to the embodiment of the present invention, having Schottky junction characteristics, a threshold voltage Vth is relatively low, and efficiency of the circuit is increased in terms of power, so that signal distortion of the gas sensor may be reduced.

Accordingly, it is determined that when the graphene-supported base substrate is used, measurement efficiency of the gas sensor is improved.

Figure 10:
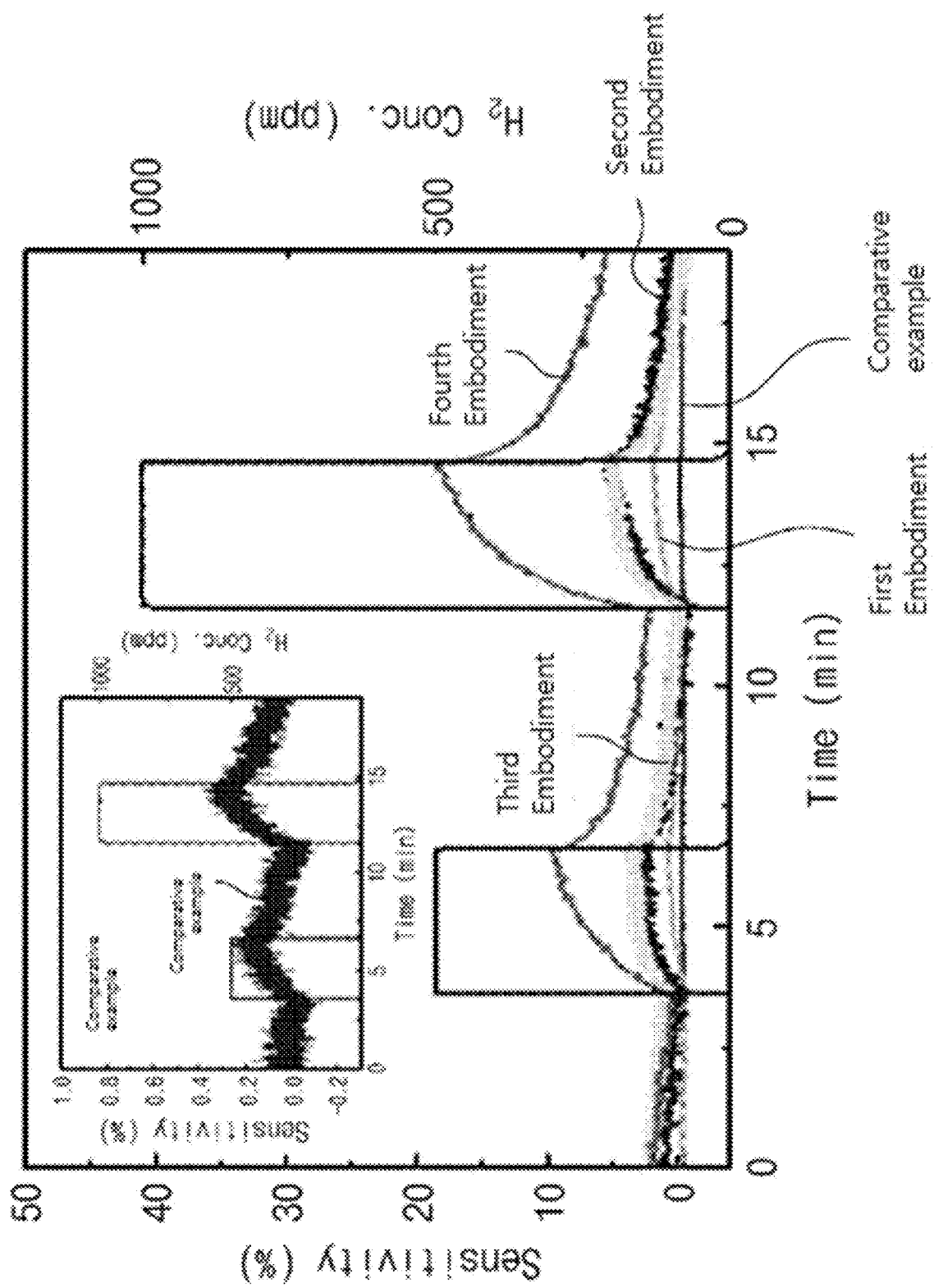
FIG. 10 is a graph depicting hydrogen gas sensing characteristics of gas sensors according to the first to fourth embodiments of the present invention and a gas sensor according to a comparative example of the embodiments in a room temperature environment.

FIG. 10 is a graph depicting hydrogen gas sensing characteristics of gas sensors according to the first to fourth embodiments of the present invention and a gas sensor according to a comparative example of the embodiments in a room temperature environment.

According to the method of manufacturing a gas sensor according to the embodiments, the gas sensors according to the first to fourth embodiments of the present invention are manufactured while the amount of the source solution provided to the porous base substrate having a thickness of 70 μm is changed.

Further, according to the method of manufacturing a gas sensor according to the comparative example, the gas sensor according to the comparative example for the embodiments of the present invention is manufactured using the porous base substrate having a thickness of 70 μm.

A voltage of 5 V is applied to the gas sensors according to the embodiments and the comparative example for the embodiments, and hydrogen gas having a concentration of 500 ppm to 1000 ppm is provided to the gas sensors at a speed of 500 sccm, so that hydrogen sensing efficiency according to whether or not the graphene is supported and the amount of the supported graphene is identified.

Referring to FIG. 10, it is identified that when the hydrogen gas is provided to the gas sensor according to the comparative example for the embodiments of the present invention, which is manufactured using only the porous base substrate in which the graphene is not supported, gas sensitivity to the hydrogen gas does not appear at the room temperature.

On the other hand, it is identified that in the case of the gas sensors according to the embodiments of the present invention, as the amount of the source solution provided to the porous base substrate increases, the gas sensitivity to hydrogen gas at the room temperature increases.

In the case of the gas sensors according to the embodiments of the present invention, using the graphene-supported base substrate, when the hydrogen gas is provided to the gas sensor, the hydrogen gas may be adsorbed to the surface of the graphene.

The adsorbed hydrogen molecules may be ionized by the oxidation-reduction reaction of [Equation 1].

$$H2 + 2\ h^+ \rightarrow 2H+ \qquad [\text{Equation 1}]$$

The carrier density of the graphene is reduced due to the above-described reaction, and thus, the electric conductivity value of the porous base substrate may be reduced.

It is determined that the types and the concentrations of various gases including the hydrogen gas may be easily measured through the change in the electric conductivity value of the graphene-supported base substrate.

FIGS. 11A to 11B are SEM images of base substrates in which graphene is supported according to the concentration of a source solution according to fifth and sixth embodiments of the present invention.

In detail, FIGS. 11A and 11B are SEM images of the graphene-supported base substrates according to the fifth and sixth embodiments of the present invention when 100 μl of the source solutions having different concentrations (0.1 mg/mL and 1 mg/ML) are provided onto the porous base substrate.

Referring to FIGS. 11A and 11B, as described above with reference to FIGS. 8A-8D, it is identified that the porous structure having a diameter of several µm is formed on the p-type silicon substrate.

Further, it is identified that as the concentration (0.1 mg/mL and 1 mg/mL) of the source solution provided onto the porous base substrate increases, the amount of the graphene supported in the porous structure of the p-type silicon substrate increases.

It can be identified that the size of the supported graphene is several µm to several tens of µm due to agglomeration.

FIG. 12 is a lateral SEM image of the graphene-supported base substrate according to the sixth embodiment of the present invention.

A lateral shape of the graphene-supported base substrate according to the sixth embodiment of the present invention, in which 100 µl of the source solution having a concentration of 1 mg/mL is provided to the porous base substrate, is identified using the scanning electron microscope (SEM) apparatus.

Referring to FIG. 12, it is identified that the supported graphene is permeated into the porous structure of the porous base substrate.

Accordingly, it is determined that since the heterostructure between the porous base substrate and the graphene is formed inside the porous structure as well as on the surface of the porous base substrate, the gas sensor according to the embodiment of the present invention has excellent sensing efficiency characteristics.

Further, it can be identified that the amount of the graphene that is a sensing substance supported in the porous structure formed on the porous base substrate may be easily controlled in a simple method of adjusting the amount of the source solution provided onto the porous base substrate.

Figure 13A:
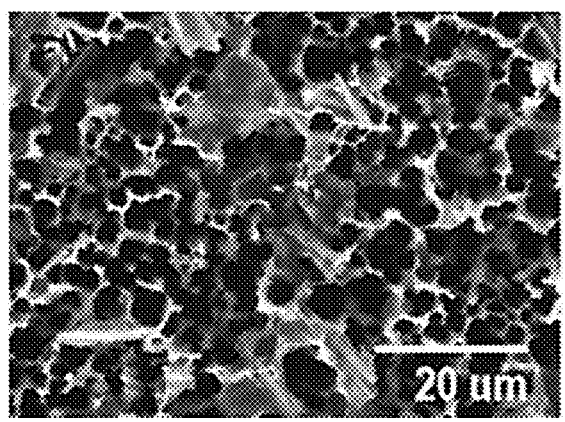
FIGS. 13A and 13B are SEM images of the graphene-supported base substrate according to the embodiment of the present invention, which is manufactured using a source solution in which a base solvent is Di-Methyl Formamide (DMF)
Figure 13B:
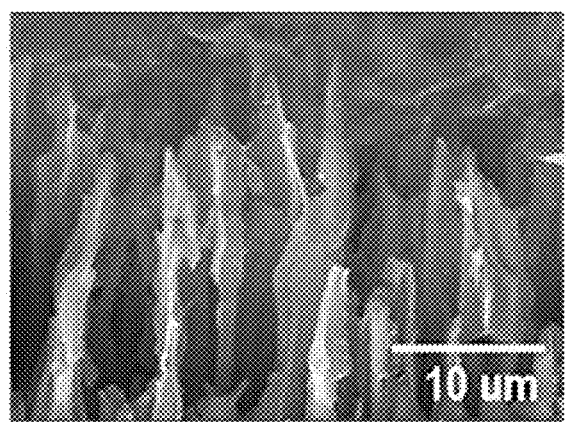

FIGS. 13A and 13B are SEM images of the graphene-supported base substrate according to the embodiment of the present invention, which is manufactured using a source solution in which a base solvent is Di-Methyl Formamide (DMF).

In detail, FIG. 13A is an SEM image of the surface of the graphene-supported base substrate according to the embodiment of the present invention, which is manufactured using the source solution in which the base solvent is the DMF, and FIG. 13B is an SEM image of the lateral surface of the graphene-supported base substrate according to the embodiment of the present invention, which is manufactured using the source solution in which the base solvent is the DMF.

When the source solution is produced according to the method of manufacturing a gas sensor according to the embodiments, in a state in which the source solution is produced by dispersing the graphene in the Di-Methyl Formamide (DMF) that is the base solvent, the graphene-supported base substrate according to the embodiment of the present invention is manufactured.

The images of the surface and the lateral surface of the graphene-supported base substrate according to the base solvent are identified using the scanning electron microscope (SEM) apparatus.

Referring to FIGS. 13A and 13B, it is identified that the supported graphene is permeated into the porous structure as well as the surface of the porous base substrate.

Figure 14A:
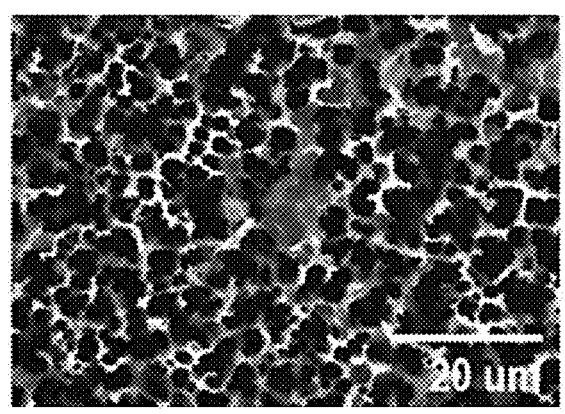
FIGS. 14A and 14B are SEM images of the graphene-supported base substrate according to the embodiment of the present invention, which is manufactured using a source solution in which a base solvent is N-Methylpyrrolidone (NMP)
Figure 14B:
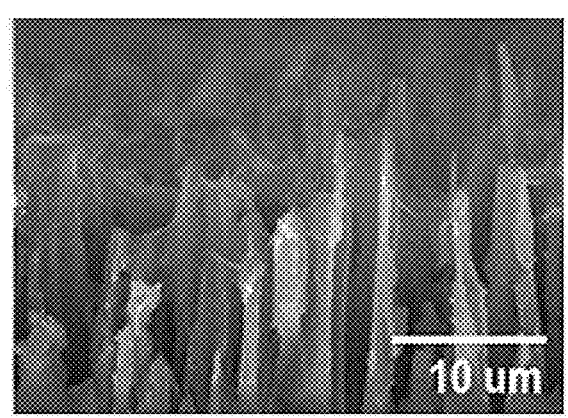

FIGS. 14A and 14B are SEM images of the graphene-supported base substrate according to the embodiment of the present invention, which is manufactured using a source solution in which a base solvent is N-Methylpyrrolidone (NMP).

In detail, FIG. 14A is an SEM image of the surface of the graphene-supported base substrate according to the embodiment of the present invention, which is manufactured using the source solution in which the base solvent is the NMP, and FIG. 14B is an SEM image of the lateral surface of the graphene-supported base substrate according to the embodiment of the present invention, which is manufactured using the source solution in which the base solvent is the NMP.

When the source solution is produced according to the method of manufacturing a gas sensor according to the embodiments, in a state in which the source solution is produced by dispersing the graphene in the N-Methylpyrrolidone (NMP) that is the base solvent, the graphene-supported base substrate according to the embodiment of the present invention is manufactured.

The images of the surface and the lateral surface of the graphene-supported base substrate according to the base solvent are identified using the scanning electron microscope (SEM) apparatus.

Referring to FIGS. 14A and 14B, similar to the result of FIG. 13, it is identified that the supported graphene is permeated into the porous structure as well as the surface of the porous base substrate.

It is determined based on the results of FIGS. 13 and 14 that since the heterostructure between the porous base substrate and the graphene is formed inside the porous structure as well as on the surface of the porous base substrate, the gas sensor according to the embodiment of the present invention has excellent sensing efficiency characteristics.

Further, it can be identified that the graphene is well supported on the porous base substrate regardless of the kind of the organic solvent used when the source solution is produced.

Figure 15:
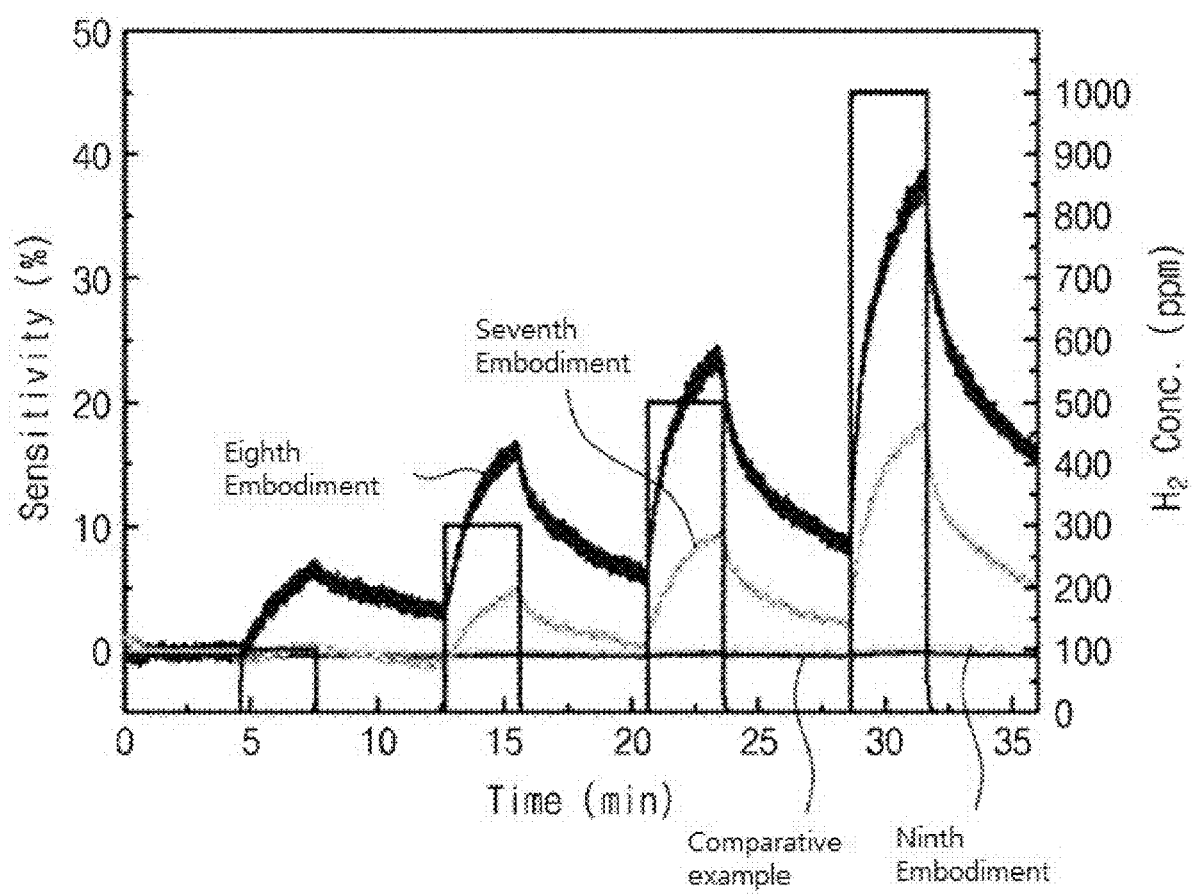
FIG. 15 is a graph depicting hydrogen gas sensing characteristics of gas sensors according to seventh to ninth embodiments of the present invention and a gas sensor according to the comparative example of the embodiments in the room temperature environment.

FIG. 15 is a graph depicting hydrogen gas sensing characteristics of gas sensors according to seventh to ninth embodiments of the present invention and a gas sensor according to the comparative example of the embodiments in the room temperature environment.

According to the method of manufacturing a gas sensor according to the embodiments, the gas sensors according to the seventh to ninth embodiments of the present invention are manufactured while the concentration (the amount of the graphene; 0.1 mg/mL (0.01 mg), 1 mg/mL (0.1 mg), and 10 mg/mL (1 mg)) of the source solution provided to the porous base substrate having a thickness of 70 µm is changed.

A voltage of 5 V is applied to the gas sensors according to the embodiments and the comparative example for the embodiments, and hydrogen gas having a concentration of 100 ppm to 1000 ppm is provided to the gas sensors at a speed of 500 sccm, so that hydrogen sensing efficiency according to whether or not the graphene is supported and the concentration and the amount of the supported graphene is identified.

Referring to FIG. 15, it is identified that the gas sensor according to the comparative example for the embodiments of the present invention, in which the graphene is not supported, sensitivity to the hydrogen gas is not exhibited in the entire range of the concentration of 100 ppm to 1000 ppm.

On the other hand, it is identified that in the gas sensor according to the seventh embodiment of the present invention in which the concentration (the amount of the graphene) of the source solution is 0.1 mg/mL (0.01 mg), sensitivity characteristics are as low as 1% to 2% when the concentration of the hydrogen gas is 100 ppm, gas sensitivity characteristics are as low as 5% when the concentration of the hydrogen gas is 300 ppm or more, and the gas sensitivity increases as the concentration of the hydrogen gas increases.

Further, it is identified that in the gas sensor according to the eighth embodiment of the present invention in which the concentration (the amount of the graphene) of the source solution is 1 mg/mL (0.1 mg), the gas sensitivity characteristics are 5% or more when the concentration of the hydrogen gas is 100 ppm, the gas sensitivity increases as the concentration of the hydrogen gas increases, and thus, the gas sensitivity characteristics are 30% or more when the concentration of the hydrogen gas is 1000 ppm.

Further, it is identified that in the gas sensor according to the ninth embodiment of the present invention in which the concentration (the amount of the graphene) of the source solution is 10 mg/mL (1 mg), similar to the comparative example for the embodiment of the present invention, sensitivity characteristics to the hydrogen gas are not exhibited in the entire range of the concentration of 100 ppm to 1000 ppm.

It can be identified based on the result of FIG. 15 that when the concentration of the source solution provided to the porous base substrate is more than 0 mg/mL and less than 10 mg/mL, a gas sensor having excellent sensing characteristics is manufactured.

In this way, it is identified that when the gas sensor is manufactured by supporting the graphene in the porous structure of the porous base substrate according to the embodiment of the present invention, the amount of the graphene supported in the gas sensor may be easily adjusted in a simple method of dropping and drying the source solution in which the graphene is dispersed onto the porous base substrate.

Further, it can be identified that sensing efficiency to the hydrogen gas may be controlled according to the amount and/or the concentration of the graphene supported on the porous base substrate.

From this, a method of manufacturing a gas sensor in which process costs and a process time are reduced because of a simplified process and which has excellent hydrogen sensing characteristics may be provided.

Although the present invention has been described above in detail with reference to exemplary embodiments of the present invention, the scope of the present invention is not limited to specific embodiments, but should be construed based on the appended claims.

Further, it is understood by those skilled in the art that various modifications and changes can be made without departing from the scope of the present invention.

INDUSTRIAL APPLICABILITY

The gas sensor according to the embodiment of the present invention and the gas sensor manufactured according to the embodiment of the present invention may be used to sense various gases such as the hydrogen gas.

What is claimed is:

1. A gas sensor comprising:
a porous base substrate comprising a porous structure;
graphene disposed within the porous structure and also disposed on a surface of the porous base substrate; and
first and second electrodes disposed on the porous base substrate,
wherein the porous structure has a form of a hole extending from an upper surface toward a lower surface of the porous base substrate, and
wherein a depletion layer and a hole accumulation layer are formed between the graphene and the porous base substrate in the hole of the porous structure.

2. The gas sensor of claim 1, wherein
the first and second electrodes are spaced apart from each other on the upper surface of the porous base substrate.

3. The gas sensor of claim 1,
wherein the target gas comprises hydrogen gas.

4. The gas sensor of claim 1, wherein
a current and voltage curve (an IV curve) of the porous base substrate forms a Schottky junction in a room temperature environment.

* * * * *